United States Patent [19]

Schultz et al.

[11] 4,044,153

[45] * Aug. 23, 1977

[54] ANTIINFLAMMATORY 2-AMINOMETHYL-6-TRIHALOMETHYL-PHENOLS

[75] Inventors: Everett M. Schultz, Ambler; Edward J. Cragoe, Jr., Lansdale, both of Pa.

[73] Assignee: Merck & Co., Inc., Rahway, N.J.

[*] Notice: The portion of the term of this patent subsequent to Feb. 26, 1991, has been disclaimed.

[21] Appl. No.: 684,138

[22] Filed: May 7, 1976

Related U.S. Application Data

[63] Continuation of Ser. No. 600,990, Aug. 1, 1975, Pat. No. 3,979,361, which is a continuation-in-part of Ser. No. 444,200, Feb. 20, 1974, abandoned, which is a continuation-in-part of Ser. No. 120,730, March 3, 1971, Pat. No. 3,794,734.

[51] Int. Cl.$^2$ .......................................... A61K 31/135
[52] U.S. Cl. .................................................... 424/330

[58] Field of Search .......................................... 424/330

[56] References Cited

U.S. PATENT DOCUMENTS

| | | | |
|---|---|---|---|
| 3,219,701 | 11/1965 | O'Shea | 260/569 |
| 3,399,226 | 11/1968 | Saari | 260/471 |
| 3,794,734 | 2/1974 | Gragoe et al. | 424/330 |
| 3,809,721 | 8/1974 | Schultz et al. | 424/330 X |
| 3,864,401 | 2/1975 | Schultz et al. | 260/570.9 |
| 3,979,361 | 9/1976 | Schultz et al. | 260/570.9 |

*Primary Examiner*—Leonard Schenkman
*Attorney, Agent, or Firm*—Mario A. Monaco; Harry E. Westlake, Jr.

[57] ABSTRACT

2-Aminomethylphenol products and their non-toxic, pharmaceutically acceptable salts useful in the treatment of edema and inflammation are disclosed. The products may be prepared by treating an N-(2-hydroxybenzyl)carboxamide with an aqueous solution of an acid or a base.

2 Claims, No Drawings

ANTIINFLAMMATORY 2-AMINOMETHYL-6-TRIHALOMETHYL-PHENOLS

CROSS-REFERENCE TO RELATED APPLICATIONS

This is a continuation, of application Ser. No. 600,990 filed Aug. 1, 1975 now U.S. Pat. No. 3,979,361, which is a continuation-in-part of co-pending application Ser. No. 444,200 filed Feb. 20, 1974, which is now abandoned, which in turn is a continuation-in-part of Ser. No. 120,730 filed Mar. 3, 1971, now U.S. Pat. No. 3,794,734.

SUMMARY OF THE INVENTION

This invention relates to 2-aminomethylphenols useful in the treatment of edema and inflammation, processes for preparing same, compositions and methods of treating inflammation. Particularly, it relates to 2-aminomethyl-4-lower alkyl-6-trihalomethylphenol or its non-toxic, pharmaceutically acceptable salts and its uses as described.

Pharmacological studies employing rats and dogs as the experimental animals indicate that the instant products and compositions containing the active products are effective diuretic and saluretic agents which can be used in the treatment of conditions associated with electrolyte and fluid retention. When administered in therapeutic dosages in conventional vehicles, the instant products effectively reduce the amount of sodium and chloride ions in the body, lower dangerous excesses of fluid level to acceptable levels and, in general, alleviate conditions usually associated with edema. Further, studies employing the mouse ear test and the carrageenin edema test commonly employed for the discovery of antiinflammatory activity such as is found in indomethacin and the antiinflammatory steroids indicate that the compounds of this invention are effective antiinflammatory agents useful both topically and systemically.

The compounds of this invention have the following formula:

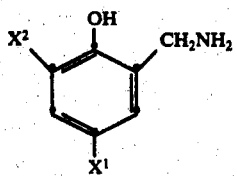

wherein
- $X^1$ is $C_{1-7}$ lower alkyl such as methyl, ethyl, n-propyl, n-butyl, sec-butyl, tert-butyl, 1-methylhexyl and the like, cycloalkyl, for example, cycloalkyl containing 5 to 6 carbon atoms such as cyclopentyl, cyclohexyl and the like;
- $X^2$ is trihalomethyl such as trifluoromethyl, trichloromethyl and the like.

Also included are their non-toxic, pharmaceutically acceptable salts, preferably the non-toxic, pharamaceutically acceptable acid addition salts derived from hydrochloric acid, hydrobromic acid, hydroiodic acid, sulfuric acid, methanesulfonic acid, isethionic acid and the like; salts may also be prepared from the alkali metal bases such as sodium hydroxide, potassium hydroxide and the like.

A preferred embodiment of this invention relates to compounds and their use having the following formula:

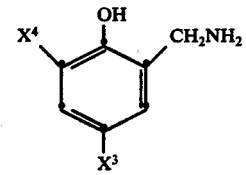

wherein
- $X^3$ is lower alkyl particularly tert-butyl; and
- $X^4$ is trifluoromethyl and the non-toxic, pharmaceutically acceptable acid addition salts thereof.

Compositions containing this class of compounds exhibit particularly good diuretic, saluretic and antiinflammatory activity and represent a preferred subgroup within the scope of the invention.

The compositions containing the 2-aminomethylphenols (I) as the active ingredient and also the 2-aminomethylphenols (I) themselves useful as diuretic and saluretic agents, can be administered in a wide variety of therapeutic dosages in conventional vehicles as, for example, by oral administration in the form of a tablet or capsules, by intravenous injection or oral solutions or suspensions. Also, the daily dosage of the products may be varied over a wide range varying from 50 to 2,000 mg. The product is preferably administered in subdivided doses in the form of scored tablets containing 5, 10, 25, 50, 100, 150, 250 and 500 milligrams of the active ingredient for the symptomatic adjustment of the dosage to the patient to be treated. An effective amount of the drug is ordinarily supplied at a dosage level of from about 1 mg. to about 50 mg./kg. of body weight. Preferably the range is from about 1 mg. to 7 mg./kg. of body weight. These dosages are well below the toxic or lethal dose of the products. A suitable suit dosage form of the products of this invention can be administered by mixing 50 milligrams of a 2-aminomethylphenol (I) or a suitable salt thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Tablets may be prepared by mixing the active ingredient with conventional tableting ingredients such as calcium phosphate, lactose, corn starch or magnesium stearate. The liquid forms in which the active ingredients may be incorporated include suitably flavored suspending or dispersing agents such as the synthetic and natural gums, for example, tragacanth, acacia, methylcellulose and the like. Other dispersing agents which may be employed include glycerin and the like. For parenteral administration sterile suspensions and solutions are desired. Isotonic preparations which generally contain a suitable preservative are employed when intravenous administration is desired.

The compositions containing the 2-aminomethylphenols as the active ingredient and also the 2-aminomethylphenols themselves, useful as topical antiinflammatory agents are particularly effective in topical treatment of dermatological disorders and like conditions, such as dermatitis (actinic, atopic, contact, eczematoid, seborrheic and stasis), dermatitis herpetiformis, lichen planus, neurodermatitis, intertrigo, lichen simplex chronicus, pruritus and psoriasis, as well as for topical treatment of inflammations of the respiratory and intestinal mucosa such as allergic rhinitis, bronchitis, bronchial asthma, bronchiectasis, colitis and the like. These 2-aminomethylphenols are ordinarily administered in the form of a pharmaceutical composition comprising the active compound in combination with a pharmacologically acceptable carrier adapted for topical administration. These topical pharmaceutical compositions may be in the form of a cream, ointment, gel or aerosol formulation adapted for application to the skin for treatment of dermatoses; or it may be in the form of a solution, suspension or aerosol adapted for topical spray application to respiratory passages for treatment of nasal allergies, bronchial inflammations, and the like; or in the form of suppositories or enclosed in enteric capsules for treatment of intestinal inflammations. For treatment of dermatological disorders, these topical pharmaceutical compositions containing the presently invented 2-aminomethylphenols ordinarily include about 0.01% to 15%, preferably about 5% of the active compound, in admixture with 95% of gel vehicle comprising water, at least one organic solvent, and at least one thickening agent. The water ordinarily constitutes from about 8% to 18% of the gel vehicle, preferably about 13%. The organic solvent ordinarily constitutes about 60% to 90% of the gel vehicle. Representative solvents are ethyl alcohol, isopropyl alcohol, propylene glycol, glycerine, 2-octyl dodecanol and methyl pyrrolidine, and preferably isopropyl alcohol; propylene glycol mixtures at a ratio of 0.5 to 0.6 parts isopropyl alcohol to 1.0 part propylene glycol. The solubility of the 2-aminomethylphenol compound in the solvent system selected should be such as to obtain maximum partitioning of the active compound from the vehicle to the skin. The thickening agent, preferably hydroxyethyl cellulose, hydroxypropyl cellulose, and the like, ordinarily constitutes from 0.5 to 4.0% of the gel vehicle. Optionally, a stabilizing agent, such as disodium edetate, sodium citrate, dipotassium edetate, citric acid, and the like, in the proportion of about 0.02% to 0.1% of the gel vehicle may be employed, if desired.

A preferred topical pharmaceutical composition is prepared as follows: About 2.60 g. of hydroxypropyl cellulose is added to a solution of 0.05 g. of disodium edetate in 13.00 g. purified water while agitating the mixture and maintaining the temperature at about 60° C., and the agitation is continued until the hydroxypropyl cellulose is completely dispersed and wetted. To the resulting dispersed mixture is added, with agitation, a solution containing 5.0 g. of, for example, 2-aminomethyl-4-t-butyl-6-trifluoromethylphenol hydrochloride dispersed in a mixture of 30.00 g. of anhydrous isopropyl alcohol and 49.35 g. of propylene glycol. The resulting gel mixture is stirred vigorously at room temperature for a period of approximately 15 minutes thereby forming a pharmaceutical composition adapted for the treatment of topical antiinflammatory conditions.

The compositions containing the 2-aminomethylphenols as the active ingredient and also the 2-aminomethylphenols themselves, useful as systemic antiinflammatory agents may be orally, rectally or parenterally administered to patients in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin and acacia. Exemplary of liquid carriers are peanut oil, olive oil, sesame oil and water. Similarly, the carrier or diluent may include a time delay material such as glyceryl monostearate or glyceryl distearate alone or with a wax.

Several pharmaceutical forms of the therapeutically useful compositions can be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, an aqueous solution or a liquid suspension. Suppositories may be prepared in a conventional manner by mixing the compounds of this invention with a suitable non-irrating excipient which is solid at room temperature, but liquid at the rectal temperature. Such materials are cocoa butter and polyethylene glycol. Gels and lotions for topical application may be prepared in a conventional manner. The active compounds are administered in an amount sufficient to treat inflammation; that is, to reduce inflammation. Advantageously, the compositions will contain the active ingredient in an amount of from about 0.1 mg. to 50 mg. per kg. body weight per day (5 mg. to 3.5 g. per patient per day), preferably from about 1 mg. to 15 mg./kg. body weight per day (50 mg. to 1 g. per patient per day).

Various tests have been carried out to show the ability of the compounds described herein to exhibit reactions that can be correlated with antiinflammatory activity in humans. One such test used is the carrageenin test which is known to correlate well with antiinflammatory activity in humans and is a standard test used to determine antiinflammatory activity. This test shows the ability of compounds to inhibit edema induced by injection of an inflammatory agent into the tissue of the foot of a rat against non-inflamed controls. This test is generally outlined by C. A. Winter, Proc. Soc. Exptl. Biolog. & Med., 1962, III, 544. The correlation has been shown by the activities of compounds known to be clinically active, including Indocin, Asprin, Butazolidin, Tandearil, Cortone, Hydrocortone, Decadron.

The following examples are illustrative of how to prepare various compositions containing the active ingredients of this invention. However, the examples are merely illustrative and should not be construed as limiting the scope of the invention.

EXAMPLE 1

Tablets containing 100 mg. of active ingredient per tablet

|  | Per Tablet |
|---|---|
| 2-Aminomethyl-4-tert-butyl-6-trifluoromethylphenol hydrochloride | 100 mg. |
| Calcium Phosphate | 40 mg. |
| Lactose | 38 mg. |
| Corn Starch | 20 mg. |
| Magnesium Stearate | 2 mg. |
|  | 200 mg. |

The 2-aminomethyl-4-tert-butyl-6-trifluoromethylphenol hydrochloride is mixed with the calcium phosphate and lactose for ten minutes and then passed through a mill to reduce the particle size. The combined ingredients are remixed for five minutes and corn starch is passed through a No. 60 sieve (U.S. Sieve Series) onto the ingredients. The combined ingredients are again remixed for five minutes and then magnesium stearate is added through a No. 60 sieve. After remixing for two minutes the ingredients are compressed into tablets.

Similar dry-filled capsules, tablets, elixirs and suspensions can be prepared by replacing the active ingredient of the above example by any of the other compounds described in the foregoing general disclosure and the specific examples which follow.

EXAMPLE 2

A mixture of 250 parts of 2-aminomethyl-4-tertbutyl-6-trifluoromethylphenol hydrochloride and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

25, 100 or 500 parts of 2-aminomethyl-4-tertbutyl-6-trifluoromethylphenol hydrochloride may be used in place of 250 parts above to produce tablets suitable for oral administration according to the method of this invention.

EXAMPLE 3

A mixture of 50 parts of 2-aminomethyl-4-methyl-6-trifluoromethylphenol hydrochloride, 3 parts of the calcium salt of lignin sulfonic acid and 237 parts of water is ball-milled until the size of substantially all of the particles is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

2-aminomethyl-4-tert-butyl-6-trichloromethylphenyl hydrochloride may be used in place of the allylamino compound in the above example to obtain a suspension suitable for oral administration.

EXAMPLE 4 1. Tablets - 10,000 scored tablets for oral use, each containing 500 mg. of active ingredient are prepared from the following ingredients:

|  | Gm. |
| --- | --- |
| 2-aminomethyl-4-tert-butyl-6-trifluoromethylphenol hydrochloride | 5000 |
| Starch, U.S.P. | 350 |
| Talc, U.S.P. | 250 |
| Calcium Stearate | 35 |

The 2-aminomethylphenol compound is granulated with a 4% w./v. aqueous solution of methylcellulose U.S.P. (1500 cps.). To the dried granules is added a mixture of the remainder of the ingredients and the final mixture compressed into tablets of proper weight. 2. Capsules - 10,000 two-piece hard gelatin capsules for oral use, each containing 250 mg. of active ingredient are prepared from the following ingredients:

|  | Gm. |
| --- | --- |
| 2-aminomethyl-4-tert-butyl-6-trifluoromethylphenol hydrochloride | 2500 |
| Lactose, U.S.P. | 1000 |
| Starch U.S.P. | 300 |
| Talc U.S.P. | 65 |
| Calcium Stearate | 25 |

The 2-aminomethyl compound is mixed with the starch lactose mixture followed by the talc and calcium stearate. The final mixture is then encapsulated in the usual manner. Capsules containing 10, 25, 50 and 100 mg. of active ingredient are also prepared by substituting 100, 250, 500 and 1000 gm. for 2500 gm. in the above formulation. 3. Soft elastic capsules - One-piece soft elastic capsules for oral use, each containing 500 mg. of active material are prepared in the usual manner by first dispersing the active material in sufficient corn oil to render the material capsulatable. 4. Aqueous suspension - An aqueous suspension for oral use containing in each 5 ml., 1 gm. of active ingredient is prepared from the following ingredients:

|  | Gm. |
| --- | --- |
| 2-aminomethyl-4-tert-butyl-6-trifluoromethylphenol hydrochloride | 2000 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D. & C. orange dye | 7.5 |
| Deionized water, q.s. to 10,000 ml. | |

EXAMPLE 5

Gel Formulation 0.1 mg. disodium edetate
13.0 mg. of purified H$_2$O
300 mg. isopropanol
26 mg. hydroxypropylcellulose
50 mg. 2-aminomethyl-4-tert-butyl-6-trifluoromethylphenol hydrochloride
q.s.a.d. 1 gm. propylene glycol

EXAMPLE 6

Ointment Formulation 50 mg. wool alcohols B.P.
150 mg. amichol C
350 mg. white wax
50 mg. 2-aminomethyl-4-tert-butyl-6-trifluoromethylphenol hydrochloride
q.s.a.d. 1 gm. isopropyl myristate The 2-aminomethylphenols (I) described above may be prepared by one of two methods which comprises (1) treating an N-(2-hydroxybenzyl)carboxamide (II) with an aqueous solution in the presence of an acid or base or (2) subjecting a substituted 2-hydroxybenzaldehyde (III) to reduction.

The first of the above-mentioned processes comprises treating an N-(2-hydroxybenzyl)carboxamide (II, infra) with an aqueous solution in the presence of an acid, preferably a mineral acid such as hydrochloric acid, hydrobromic acid, sulfuric acid, hydroiodic acid and the like; in addition to the mineral acids, bases may also be employed, for example, the alkali metal bases such as sodium hydroxide, potassium hydroxide and the like. Any solvent which is inert or substantially inert to the reactants may be employed such as ethanol, acetic acid and the like. The reaction may be conducted at a temperature in the range of from about 20° C. to about 110° C. for a period of time of from about 15 minutes to above five hours; however, the reaction is generally conducted at the reflux temperature of the particular solvent employed for a period of time of about one and one-half hours. The following equation illustrates this reaction employing a mineral acid, $HR^1$, such as hydrochloric acid, hydrobromic acid, hydroiodic acid, sulfuric acid and the like.

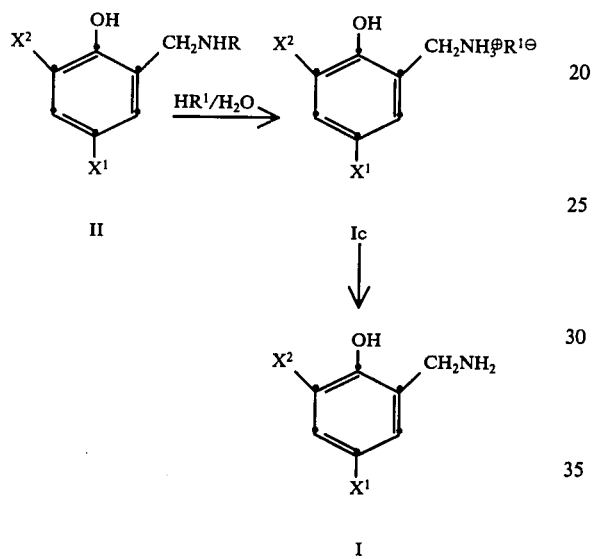

wherein $X^1$ and $X^2$ are as defined for Formula I above; R is an acyl radical, for example, ($C_{1-5}$ alkanoyl), formyl, haloacetyl such as chloroacetyl and the like, carbamoyl, mononuclear aroyl such as benzoyl and the like, hydroxy substituted mononuclear aroyl such as o-hydroxybenzoyl and the like or trihalomethylcarbonyl such as trichloromethylcarbonyl and the like and $R^{1-}$ is the anion derived from an acid, for example, a mineral acid such as hydrochloric acid, hydrobromic acid, hydroiodic acid, sulfuric acid and the like. The product is usually obtained in the form of an acid addition salt and the free amine can be generated by known neutralization methods.

The second method for preparing the 2-aminomethylphenols (I) comprises subjecting a substituted 2-hydroxybenzaldoxime (III, infra) to reduction, for example, by hydrogenation such as catalytic hydrogenation employing a noble metal such as rhodium, ruthenium and the like, preferably on a carrier such as carbon and the like. The reduction is generally conducted employing as the solvent a lower alkanol such as ethanol, methanol and the like in the presence of mineral acid such as sulfuric acid and the like. The following equation illustrates this process:

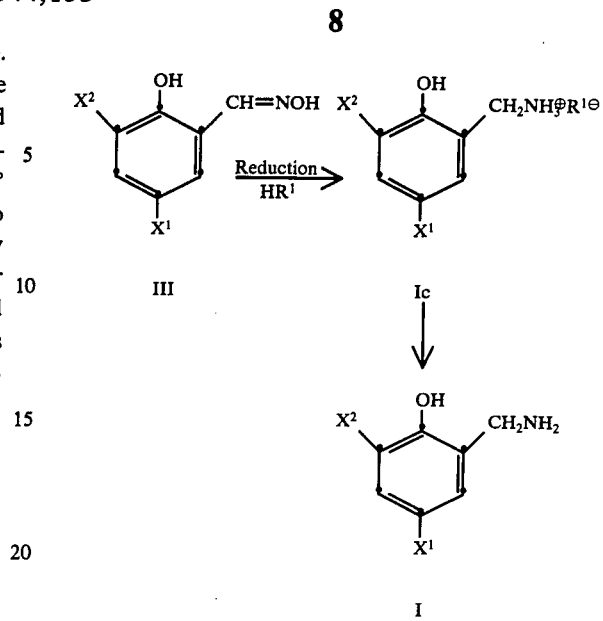

wherein $X^1$ and $X^2$ and $R^{1-}$ are as defined above. The product is usually obtained in the form of an acid addition salt and the free amine can be generated by known neutralization methods.

The N-(2-hydroxybenzyl)carboxamides (II, supra) employed as starting materials in the preparation of the 2-aminomethylphenols (I) are prepared by treating an appropriately substituted phenol (IV, infra) with an N-hydroxymethylcarboxamide, for example, N-hydroxymethylurea, 2-halo-N-hydroxymethylacetamide such as 2-chloro-N-hydroxymethylacetamide and the like, N-hydroxymethyl mononuclear arylcarboxamide such as N-hydroxymethylbenzamide and the like, N-hydroxymethyl hydroxy substituted arylcarboxamide such as N-hydroxymethylsalicylamide and the like or N-hydroxymethyltrihaloacetamide such as N-hydroxymethyltrichloroacetamide and the like in the presence of a strong mineral acid such as hydrochloric acid, sulfuric acid and the like. The reaction may be conducted employing as the solvent an excess of the mineral acid employed or with a solvent which is inert or substantially inert to the reactants employed, for example, a lower alkanol such as ethanol and the like or a lower alkanoic acid such as acetic acid and the like. The N-(2-hydroxybenzyl)carboxamides (II) may be isolated and purified; however, it has been found that by employing the crude N-(2-hydroxybenzyl)carboxamides satisfactory results are obtained. The following equation illustrates this process:

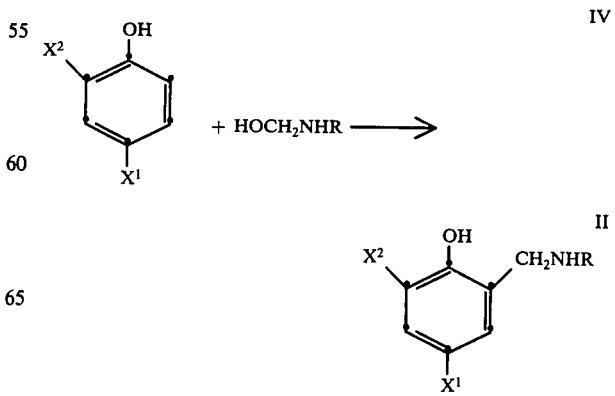

wherein $X^1$, $X^2$ and R are as defined above.

The 2-hydroxybenzaldoximes (III, supra) employed may be prepared by treating an appropriate phenol with chloroform in the presence of a base or a mixture of bases such as sodium carbonate and calcium hydroxide which yields the correspondingly substituted 2-hydroxybenzaldehyde then the 2-hydroxybenzaldehyde (V, infra) is treated with a hydroxylamine hydrohalide such as hydroxylamine hydrochloride and the like in the presence of a base such as sodium acetate and the like. This reaction is generally conducted in a lower alkanol solvent such as ethanol and the like. The reaction is conveniently conducted at the boiling point of the particular solvent employed. The following equation illustrates this process:

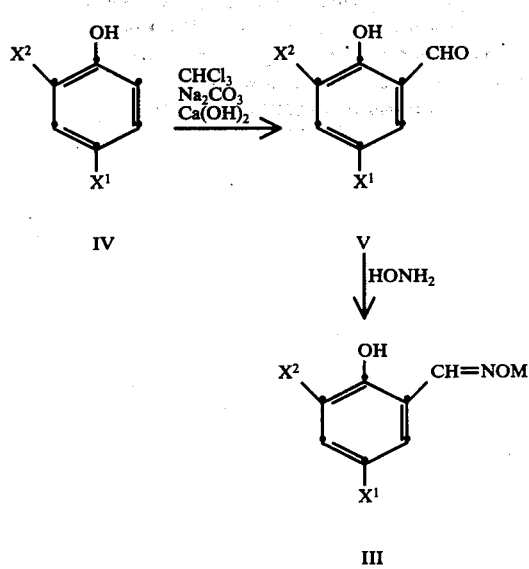

wherein $X^1$ and $X^2$ are as defined above.

The following examples illustrates the preparation of the 2-aminomethylphenols (I). However, the examples are illustrative only and it will be apparent to those having ordinary skills in the art that all of the products embraced by Formula I, supra, may also be prepared in an analogous manner by substituting the appropriate starting materials for those set forth in the examples.

EXAMPLE 7

Preparation of 2-aminomethyl-4-tert-butyl-6-trifluoromethylphenol hydrochloride

A. Preparation of 2-trifluoromethyl-4-tert-butylphenol

A mixture of 2-rifluoromethylphenol (25 g., 0.15 moles), tert-butyl alcohol (12 g., 0.16 mole), trifluoroacetic acid (100 ml.) and 96% sulfuric acid (2 ml.) is stirred at about 20° C for 48 hours. The mixture then is evaporated as far as possible under reduced pressure at 35°-40° C. The residue is dissolved in benzene (500 ml.) and the solution is washed with water, saturated NaHCO₃ solution and saturated salt brine and dried over anhydrous Mg SO₄. The dried solution is again evaporated under reduced pressure and the temperature is finally raised to 140°-150° C under 65 mm. pressure to remove unchanged 2-trifluoromethylphenol. The residue is distilled at 65 mm. after collecting a small forerun (75% unchanged starting phenol and 25% product), 2-trifluoromethyl-4-tert-butylphenol (13.6 g) is collected at 120°-132° C as a pale pink oil that is 98% pure by gas liquid chromatography analysis and can be used directly in the next step.

Following the above procedure but using an equivalent amount of isopropyl alcohol, sec-butyl alcohol or cyclohexyl alcohol in place of tert-butyl alcohol, there is produced an equivalent amount of 2-trifluoromethyl-4-isopropylphenol, 2-trifluoromethyl-4-sec-butylphenol or 2-trifluoromethyl-4-cyclohexylphenol.

B. Preparation of 2-aminomethyl-4-tert-butyl-6-trifluoromethylphenol hydrochloride 2-Trifluoromethyl-4-tert-butylphenol (15.6 g., 0.062 mole) is dissolved in a mixture of glacial acetic acid (200 ml.) and 96% sulfuric acid (150 ml.). The mixture is stirred and finely powdered N-hydroxymethyl-2-chloroacetamide (8 g., 0.065 mole) is added in small portions at 20°-25° C. Stirring then is continued for 5 hours after which the mixture is poured into water (3 l.). The 2-(2-chloroacetamidomethyl)-4-tert-butyl-6-iodophenol that separates is collected and dried by suction to obtain a solid (19 g., m.p. about 85°-100° C).

The solid, the 2-chloroacetyl derivatives of 2-aminomethyl-4-tert-butyl-6-trifluoromethylphenol hydrochloride, is dissolved in a mixture of ethanol (75 ml.) and 12 N hydrochloric acid (25 ml.). The mixture is refluxed for 5 hours, cooled to 20° C and diluted with 12 N hydrochloric acid (150 ml.). Upon cooling to −20° C, the product separates (14 g.). It is crystallized from ethanol-12 N hydrochloric acid (1:4) to obtain pure 2-aminomethyl-4-tert-butyl-6-trifluoromethylphenol hydrochloride, m.p. 202°-204° C.

Anal. Calc.: C,50.80; H,6.04; N,4.94. Found: C,50.75; H,6.01; N,4.72.

Following the above procedure but using an equivalent amount of 2-trifluoromethyl-4-isopropylphenol, 2-trifluoromethyl-4-sec-butylphenol or 2-trifluoromethyl-4-cyclohexylphenol in place of 2-trifluoromethyl-4-tert-butylphenol, there is obtained an equivalent amount of 2-aminomethyl-4-isopropyl-6-trifluoromethylphenol hydrochloride, 2-aminomethyl-4-sec-butyl-6-trifluoromethylphenol hydrochloride or 2-aminomethyl-4-cyclohexyl-6-trifluoromethylphenol hydrochloride.

EXAMPLE 8

2-Aminomethyl-4-tert-butyl-6-trifluoromethylphenol hydrochloride

A. 3-Trifluoromethyl-5-tert-butyl salicylaldehyde 0.1 mole of 2-trifluoromethyl-4-tert-butylphenol and 0.1 mole of hexamethylenetretramine is dissolved in trifluoroacetic acid (150 ml.) and the mixture refluxed for 8 hours. After this time, 150 ml. of water and 50 ml. of concentrated hydrochloric acid is added. This mixture is then refluxed for ½ hour. The reaction mixture is cooled and extracted with ether (5 × 50 ml.) and the ether extract is dried over magnesium sulfate. The ether is evaporated and the residue is crystallized from ethanol to yield 3-trifluoromethyl-5-t-butyl salicylaldehyde.

B. 3-Trifluoromethyl-5-tert-butyl salicylaldehyde oxime 0.05 moles of the aldehyde from Step A, 0.12 moles of hydroxylamine hydrochloride and sodium acetate (0.12 moles) are dissolved in a mixture of ethanol (100 ml.) and water (30 ml.). The reaction mixture is refluxed for 2 hours, cooled and water added until no more precipitate forms. The solid that separates is crystallized from ethanol to yield 3-trifluoromethyl-5-tert-butyl salicylaldehyde oxime.

C.
2-Aminomethyl-4-tert-butyl-6-trifluoromethylphenol hydrochloride

The oxime of Step B (0.02 moles) is dissolved in ethanol (200 ml.) to which concentrated $H_2SO_4$ (0.05 moles) is added. To this solution is added 5% Ruthenium on carbon (100 mg.). The mixture is hydrogenated at 40 lbs./sq. in. until the calculated amount of hydrogen is taken up. The catalyst is removed by filtration and the filtrate is evaporated to dryness, giving the sulphate salt of the title compound. The sulfate is suspended in water and neutralized with 28% ammonium hydroxide. The free base is taken up in ethanol and an equivalent amount of 6N ethanolic HCl is added. On addition of ether the title product is precipitated. The precipitate is collected and crystallized from a mixture of ethanol and concenrated HCl.

What is claimed is:
1. A pharamaceutical composition comprising an antiinflammatory effective amount of a compound of the formula:

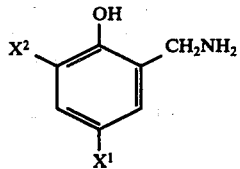

wherein $X^1$ is $C_{1-7}$ lower alkyl, or cycloalkyl containing 5 to 6 carbon atoms; and $X^2$ is trifluoromethyl; or the non-toxic pharmaceutically acceptable salts thereof in a pharamceutically acceptable carrier.

2. The composition of claim 1 wherein $X^1$ is tert-butyl.

* * * * *